United States Patent
Iwaki et al.

(10) Patent No.: US 8,579,441 B2
(45) Date of Patent: Nov. 12, 2013

(54) MEASUREMENT DEVICE AND MEASUREMENT METHOD FOR FLICKERING PERCEPTION THRESHOLD

(75) Inventors: Sunao Iwaki, Ikeda (JP); Nobuyoshi Harada, Ikeda (JP); Kouichi Sutani, Ikeda (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 90 days.

(21) Appl. No.: 13/395,178

(22) PCT Filed: Jul. 20, 2010

(86) PCT No.: PCT/JP2010/062196
§ 371 (c)(1),
(2), (4) Date: Mar. 9, 2012

(87) PCT Pub. No.: WO2011/030622
PCT Pub. Date: Mar. 17, 2011

(65) Prior Publication Data
US 2012/0169997 A1    Jul. 5, 2012

(30) Foreign Application Priority Data

Sep. 10, 2009 (JP) ................... 2009-209223

(51) Int. Cl.
*A61B 3/10* (2006.01)
*A61B 3/02* (2006.01)
(52) U.S. Cl.
USPC .......................................... 351/239; 351/221
(58) Field of Classification Search
USPC ........................ 351/203, 206, 222, 239, 246
See application file for complete search history.

(56) References Cited

U.S. PATENT DOCUMENTS

2010/0041002 A1    2/2010   Harada et al.

FOREIGN PATENT DOCUMENTS

| JP | 10-229981 A    | 9/1998  |
| JP | 2005-348936 A  | 12/2005 |
| JP | 2008-220639 A  | 9/2008  |

OTHER PUBLICATIONS

International Search Report of PCT/JP2010/062196, mailing date of Aug. 10, 2010.

*Primary Examiner* — Mahidere Sahle
(74) *Attorney, Agent, or Firm* — Westerman, Hattori, Daniels & Adrian, LLP

(57) ABSTRACT

The measurement method involves a step for displaying on a display screen an image in which one corresponding region exclusively that has been selected from regions provided has a contrast difference when on and when off; a step for enlarging the contrast difference in the image display in cases which an operation for an operation unit accompanying the flickering perception of a subject is assessed to not be correctly specifying the one aforementioned selected region, and, in cases which a correct specification has been assessed, recording the contrast difference at that point in a recording unit as the measurement contrast difference; and a step for assessing whether the aforementioned recorded measurement contrast difference has converged, reducing the contrast difference when convergence has not been assessed, and determining the convergence value of the aforementioned measurement contrast difference as information corresponding to the flickering perception threshold when convergence has been assessed.

18 Claims, 6 Drawing Sheets

The process is repeated until the value is converged.

(a)          (b)

MEASUREMENT DEVICE AND MEASUREMENT METHOD FOR FLICKERING PERCEPTION THRESHOLD

TECHNICAL FIELD

The present invention relates to the measurement of a threshold at which a person begins to recognize flicker. The present invention particularly relates to a measurement device and a measurement method that are capable of easily and objectively measuring a flicker perception threshold without arbitrariness or inclination; and that are applicable to the evaluation of human mental fatigue (hereunder, this may simply be referred to as "fatigue").

BACKGROUND ART

The modern world is called a stressful society, and there has been a strong demand for a method for objective fatigue measurement or evaluation for everyday use. In the past, quantitative fatigue evaluation (flicker test) was performed based on a phenomena in which the perception of "flicker" upon observation of a blinking light source changes depending on the fatigue degree; in particular, a phenomena in which the blinking frequency (Critical Flicker Frequency: CFF), which denotes the capability of perceiving a flicker, decreases along with an increase of fatigue degree. Heretofore, quantitative evaluation of fatigue degree using a flicker test has been widely employed, particularly in the industrial hygiene field. However, because this flicker test requires a dedicated device equipped with an LED or the like, it was not suitable for a universal or everyday use device.

Under such circumstances, the inventors of the present invention developed a technology for enabling a fatigue degree test, which is based on the same flicker perception principle as in the flicker test, but which uses an image-displaying device such as a CRT or a liquid crystal display (see Patent Literature 1 below). The development of such a device enables, in principle, easy fatigue measurement on a daily basis using easily accessible devices, such as mobile phones or personal computers.

CITATION LIST

Patent Literature

Japanese Unexamined Patent Publication No. 2008-220639

SUMMARY OF INVENTION

Technical Problem

In the aforementioned method used in a hitherto known flicker test, the threshold of CFF or the like was measured by gradually increasing the light-blinking cycle of a flicker; in other words, gradually decreasing the blinking frequency, and making the test subject subjectively signal the perception of "flicker" using a push-button indicator or the like.

FIG. 1 shows a concept of the aforementioned hitherto known technique for measuring a flicker threshold. In the known method, the frequency was monotonically changed, and the frequency at the time where the test subject subjectively signaled the perception of "flicker" using a push-button indicator was measured. The measured thresholds obtained from multiple tests were averaged to determine the flicker threshold.

However, since this flicker-displaying test uses a monotonous blinking light condition, after several tests, the test subject becomes able to empirically predict the result; i.e., the test subject can empirically predict the timing of flicker perception during the test. In addition, since the test result relied on the subjective perception by the test subject, there was no evidence to show that the user actually perceived the flicker. Therefore, the test subject can arbitrarily control the test result by empirically adjusting the timing of pushing the button. Further, since there were no standards for true/false answers regarding "flicker perception," the perception timing (timing of pushing a button) by the test subjects was often arbitrary, thereby varying the test results. Moreover, because this test tends to force the test subject to watch a flicker of an evidently unrecognizable frequency for a long time, the test time was prolonged; additionally, the fatigue level was often underestimated.

As such, in the known measurement method, the timing of pushing the button is likely to be influenced by the arbitrariness and inclination of the test subject; therefore, in this method, it was difficult to perform an objective measurement of a flicker perception threshold.

The present invention was made to solve the aforementioned problems of hitherto known technologies, and provides a device and a method for the measurement of flicker perception threshold; the device and the method being capable of objectively measuring an accurate flicker perception threshold while eliminating arbitrariness or inclination of the test subject, thereby accurately evaluating mental fatigue of human.

Solution to Problem

The objective of the present invention is accomplished by the following means.

Specifically, a method (1) for measuring a flicker perception threshold according to the present invention is a method for measuring a flicker perception threshold using a device comprising an operation unit, a display screen, and a recording unit, the method comprising:

a first step of alternately displaying on the display screen an ON-period image and an OFF-period image each having a plurality of regions, the ON-period image and the OFF-period image having a contrast difference only in one corresponding region selected from the plurality of regions;

a second step of, when it is judged during display of the ON and OFF-period images that an operation in the operation unit that is made by a test subject in response to perception of a flicker does not properly specify the one corresponding region, increasing the contrast difference, and when it is judged that the operation in the operation unit properly specifies the one corresponding region, recording the contrast difference at the time in the recording unit as a measured contrast difference; and a third step of judging whether the measured contrast difference recorded in the recording unit is converged; when it is judged that the measured contrast difference is not converged, decreasing the contrast difference, and when it is judged that the measured contrast difference is converged, determining a convergence value of the measured contrast difference as information corresponding to the flicker perception threshold.

A method (2) for measuring a flicker perception threshold according to the present invention is a method for measuring a flicker perception threshold using a device method for measuring a flicker perception threshold using a device comprising an operation unit, a display screen, and a recording unit,
the method comprising:
a first step of blinking one region selected from a plurality of regions of the display screen at a first blinking frequency, and blinking other regions of the display screen at a second blinking frequency that cannot be perceived by human,
a second step of, when it is judged during the blinking that an operation in the operation unit that is made by a test subject in response to perception of a flicker in the display screen does not properly specify the one region, decreasing the first blinking frequency, and when it is judged that the operation in the operation unit properly specifies the one region, recording the first blinking frequency at the time in the recording unit as a measured blinking frequency; and
a third step of judging whether the measured blinking frequency recorded in the recording unit is converged; when it is judged that the measured blinking frequency is not converged, increasing the first blinking frequency, and when it is judged that the measured blinking frequency is converged, determining a convergence value of the measured blinking frequency as information corresponding to the flicker perception threshold.

A method (3) for measuring a flicker perception threshold according to the present invention is a method for measuring a flicker perception threshold using a device comprising an operation unit, a plurality of groups of one or more light-emitting elements disposed in a plurality of regions, and a recording unit,
the method comprising:
A first step of blinking one or more light-emitting elements disposed in a region selected from the plurality of regions at a first blinking frequency, and blinking other light-emitting elements at a second blinking frequency that cannot be perceived by human,
a second step of, when it is judged during the blinking that an operation in the operation unit that is made by a test subject in response to perception of a flicker of the light-emitting elements does not properly specify the one or more light-emitting elements in the region, decreasing the first blinking frequency, and when it is judged that the operation in the operation unit properly specifies the one or more light-emitting elements in the region, recording the first blinking frequency at the time in the recording unit as a measured blinking frequency; and
a third step of judging whether the measured blinking frequency recorded in the recording unit is converged; when it is judged that the measured blinking frequency is not converged, increasing the first blinking frequency, and when it is judged that the measured blinking frequency is converged, determining a convergence value of the measured blinking frequency as information corresponding to the flicker perception threshold.

The above methods (1) to (3) may be arranged such that the plurality of regions are separated from each other.

The above methods (1) to (3) may be arranged such that the one region selected from the plurality of regions represents a number or a graphic, and the step of specifying the region is a step of specifying the number or the graphic.

A device (1) for measuring a flicker perception threshold according to the present invention is a device comprising an arithmetic processing unit, a display screen, an operation unit, and a recording unit,
wherein:
the arithmetic processing unit alternately displays on the display screen an ON-period image and an OFF-period image each having a plurality of regions, the ON-period image and the OFF-period having a contrast difference in only one corresponding region selected from the plurality of regions;
when it is judged during display of the ON and OFF-period images that an operation in the operation unit that is made by a test subject in response to perception of a flicker does not properly specify the one corresponding region, the arithmetic processing unit increases the contrast difference, and when it is judged that the operation in the operation unit properly specifies the one corresponding region, the arithmetic processing unit records the contrast difference at the time in the recording unit as a measured contrast difference; and
the arithmetic processing unit judges whether the measured contrast difference recorded in the recording unit is converged; when it is judged that the measured contrast difference is not converged, the arithmetic processing unit decreases the contrast difference, and when it is judged that the measured contrast difference is converged, the arithmetic processing unit determines a convergence value of the measured contrast difference as information corresponding to the flicker perception threshold.

A device (2) for measuring a flicker perception threshold according to the present invention is a device comprising an arithmetic processing unit, a display screen, an operation unit, and a recording unit,
wherein:
the arithmetic processing unit blinks the one region selected from a plurality of regions of the display screen at a first blinking frequency, and blinks other regions at a second blinking frequency that cannot be perceived by human,
when it is judged during the blinking that an operation in the operation unit that is made by a test subject in response to perception of a flicker in the display screen does not properly specify the one region, the arithmetic processing unit decreases the first blinking frequency, and when it is judged that the operation in the operation unit properly specifies the one region, the arithmetic processing unit records the first blinking frequency at the time in the recording unit as a measured blinking frequency; and
the arithmetic processing unit judges whether the measured blinking frequency recorded in the recording unit is converged; when it is judged that the measured blinking frequency is not converged, the arithmetic processing unit increases the first blinking frequency, and when it is judged that the measured contrast difference is converged, the arithmetic processing unit determines a convergence value of the measured blinking frequency as information corresponding to the flicker perception threshold.

A device (3) for measuring a flicker perception threshold according to the present invention is a device comprising an arithmetic processing unit, an operation unit, a plurality of groups of one or more light-emitting elements disposed in a plurality of regions, and a recording unit,
wherein:
the arithmetic processing unit blinks one or more light-emitting elements disposed in the region selected from the plurality of regions at a first blinking frequency, and blinking other light-emitting elements at a second blinking frequency that cannot be perceived by human,
when it is judged during the blinking that an operation in the operation unit that is made by a test subject in response to perception of a flicker of the light-emitting elements does not properly specify the one or more light-emitting elements in the region, the arithmetic processing unit decreases the first blinking frequency, and when it is judged that the operation in the operation unit properly specifies the one or more light-emitting elements in the region, the arithmetic processing unit records the first blinking frequency at the time in the recording unit as a measured blinking frequency; and the arithmetic processing unit judges whether the measured blinking frequency recorded in the recording unit is converged; when it is judged that the measured blinking frequency is not converged, the arithmetic processing unit increases the first blinking frequency, and when it is judged that the measured blinking frequency is converged, the arithmetic processing unit determines a convergence value of the measured blinking frequency as information corresponding to the flicker perception threshold.

The above device (1) to (3) may be arranged such that the plurality of regions are separated from each other.

The above device (1) to (3) may be arranged such that the one region selected from the plurality of regions represents a number or a graphic, and the step of specifying the region is a step of specifying the number or the graphic.

Advantageous Effects of Invention

The present invention makes it possible to determine whether the reaction of the test subject upon perception of a visual stimulation is appropriate, and control the contrast difference (or normalized contrast) or frequency based on the determination result, thereby eliminating arbitrariness or inclination of the test subject. With this characteristic, the present invention more objectively measures a flicker perception threshold. Accordingly, it becomes possible to more objectively evaluate mental fatigue of human.

In particular, the hitherto known test cannot prevent excessive fatigue or an accident due to fatigue, because the test subject can intentionally provide a false non-fatigue result even though they are actually tired. In contrast, since the present invention can prevent such an intentional false result, it is useful for self-health management, as well as for labor management or safety management of production workers.

Moreover, by adopting a perception threshold determining method in which the value converges to the perception threshold in the variation control for a contrast difference (or normalized contrast) or a frequency, it becomes possible to more accurately determine a flicker perception threshold in a short time, compared to the known method. More specifically, the present invention reduces the test time, and thereby further increases the convenience of the test.

DESCRIPTION OF EMBODIMENTS

Embodiments of the present invention are described below in reference to the attached drawings. Hereinafter, "fatigue" means mental fatigue, unless otherwise specified.

First Embodiment

Figure 1:
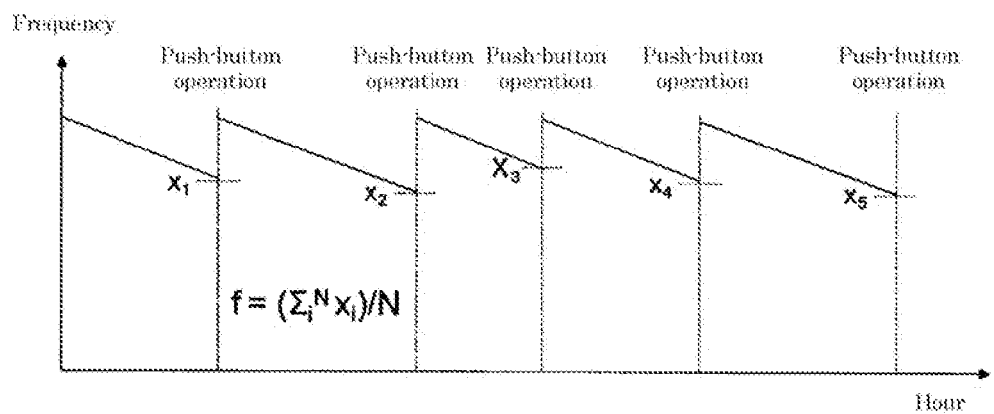
FIG. 1 A drawing showing a concept of measurement of a flicker perception threshold in the hitherto known technology.
Figure 2:
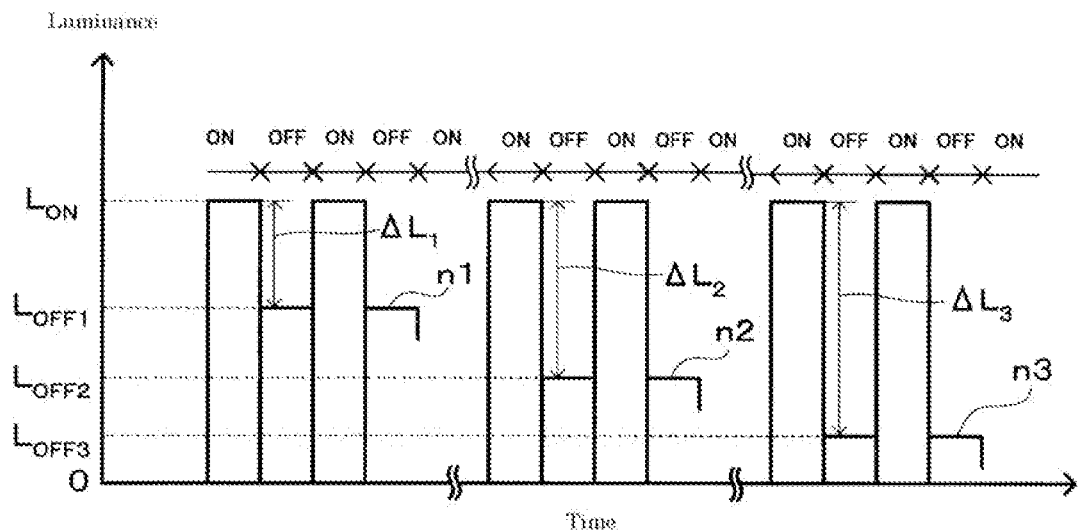
FIG. 2 A drawing showing a normalized contrast and a contrast difference.

When a display apparatus displays an image at a fixed refresh rate, the luminance ratio ($L_{OFF}/L_{ON}$) of the image between the OFF state and the ON state is defined as a normalized contrast (see FIG. 2). When an image is continuously displayed while gradually decreasing the normalized contrast, for example, as shown in n1 to n3 in FIG. 2, the test subject perceives a flicker at a point where the normalized contrast becomes equal to or below a certain threshold. By making the test subject react to notify the perception using push-button operation or the like when the test subject subjectively perceives a "flicker," it is possible to define this threshold as information corresponding to a flicker perception threshold. Moreover, when an image is continuously displayed while gradually increasing the normalized contrast, for example, from zero, the test subject stops perceiving the flicker when the normalized contrast becomes equal to or greater than a certain threshold. As above, by making the test subject react to notify the inability to perceive the flicker using a push-button operation or the like when the test subject becomes unable to perceive a "flicker," it is possible to define this threshold as information corresponding to a flicker perception threshold.

Further, this threshold decreases in proportion to an increase in fatigue level of the test subject.

In the present embodiment, when an image is presented to a test subject, a visual stimulation is generated by turning the image on and off while inducing a contrast difference (an example is shown in ΔL1 in FIG. 2) in a part of the image. The information regarding the part (hereinafter referred to as a visual stimulation region) of the image is recorded, and judgment is carried out as to whether the reaction of the test subject regarding the perception of a flicker is appropriate based on the information regarding the visual stimulation region; then, according to the true/false judgment of the reaction of the test subject, the visual stimulation region and the contrast difference are changed. Further, to change the visual stimulation region and the contrast difference, a perception threshold determination method in which the value converges to the perception threshold is employed. This eliminates arbitrariness and inclination of the test subject during the test, thereby enabling a measurement of flicker threshold in a short time based on objective flicker perception.

The normalized contrast of two images, i.e., an image in the OFF state and an image in the ON state, is in inverse proportion to the contrast difference of the two images. In particular, when the contrast (or a luminance value) in the ON state is fixed, the relationship between the normalized contrast and the contrast difference is uniquely determined. As the normalized contrast increases, the contrast difference decreases; and as the normalized contrast decreases, the contrast difference increases. Therefore, in the present specification, a control to decrease the normalized contrast is equal to a control to increase the contrast difference. In other words, a control to increase the normalized contrast is equal to a control to decrease the contrast difference.

More specifically, the two terms are interchangeable according to the circumstances. However, in this specification, the term "normalized contrast" is used in the comparison with the CCF threshold of the hitherto known flicker test apparatus, and "contrast difference" is used to more clearly explain the present invention.

Figure 3:
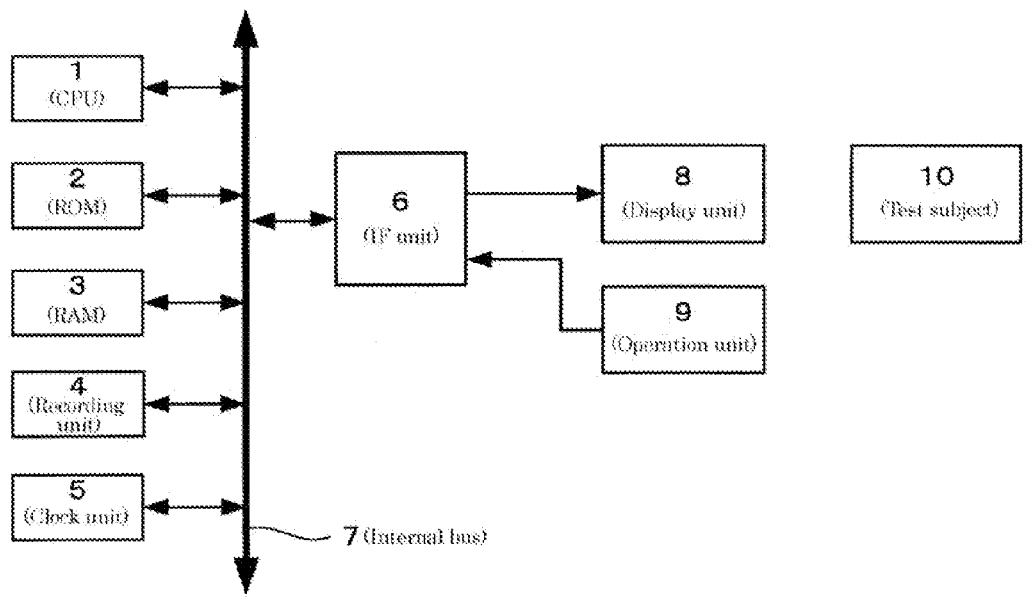
FIG. 3 A block diagram showing a flicker perception threshold measurement device according to an embodiment of the present invention.

FIG. 3 is a block diagram showing a flicker perception threshold measurement device according to the First Embodiment of the present invention.

The measurement device of the present invention comprises an arithmetic processing unit (hereinafter referred to as a CPU) 1 for controlling the entire apparatus; a nonvolatile read-only memory (hereinafter referred to as a ROM) 2 for storing a program, etc.; a volatile rewritable memory (hereinafter referred to as a RAM) 3 for temporarily storing data; a nonvolatile rewritable recording unit 4 for continuously storing data; a clock unit 5; an interface unit (hereinafter referred to as an IF unit) 6 for interfacing with external apparatuses; an internal bus 7 for exchanging data (including control information) between the units; a display unit 8; and an operation unit 9. For example, a known computer or mobile device (mobile phone, PHS, PDA, etc.) can be used as the present measurement device of the present invention.

The operation unit 9 includes operating means such as keys or pads. The display unit 8 includes a display screen (such as a liquid crystal display) and a drive unit for driving the display. The clock unit 5 is means for outputting current time information using an internal clock, such as a timer.

The following briefly describes the operation of the present measurement device. The CPU 1 randomly specifies a predetermined region as region information in an image having two or more regions, stores the information in the recording unit 4, and generates two image data items according to previously specified conditions. These two image data items have a contrast difference in the respective aforementioned predetermined regions, and have the same contrast in the rest of the regions. The CPU 1 sends the two image data items to the display unit 8 via the IF unit 6, and displays the two images respectively in the ON and OFF times. The signal supplied to the display unit 8 is digital data or an analog video signal converted by the IF unit. The display unit 8 displays the received image data to a test subject 10 at a predetermined refresh rate. The test subject 10 observes the image presented in the display screen of the display unit 8, and operates the operation unit 9 to specify a certain region in the image when they recognize the appearance or disappearance of a flicker in the region. This operation information is sent to the CPU 1 via the IF unit 6, and is recorded in the RAM 3 or the recording unit 4. The CPU 1 carries out a judgment as to whether the region specified by the test subject is identical to the predetermined region stored as the region information. When they are identical, in other words, when the test subject properly specifies a flicker region, the CPU 1 generates an image again with a smaller contrast difference, and displays the image to the test subject. When they are not identical, in other words, when the test subject improperly specifies a flicker region, the CPU 1 generates an image again with a greater contrast difference, and displays the image to the test subject.

As such, a judgment is carried out as to whether the test subject properly perceives a flicker by irregularly changing the image display state. In the present invention, instead of monotonously increasing or decreasing the normalized contrast between the images and storing the normalized contrast at the time when the test subject perceives a flicker, the normalized contrast (contrast difference) of the displayed images and a flicker region are irregularly changed, and the convergence value of the normalized contrast (contrast difference) at which the condition where the test subject perceives the appearance or disappearance of flicker is stably converged is determined as a flicker perception threshold.

Figure 4:
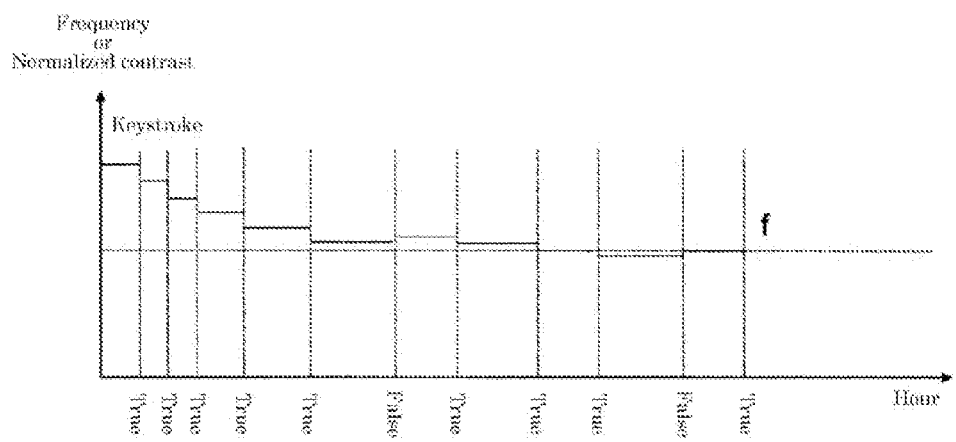
FIG. 4 A drawing showing a concept of measurement of a flicker perception threshold according to the present invention.

FIG. 4 is a drawing showing a concept of measurement of a flicker perception threshold according to the present invention.

Figure 5:
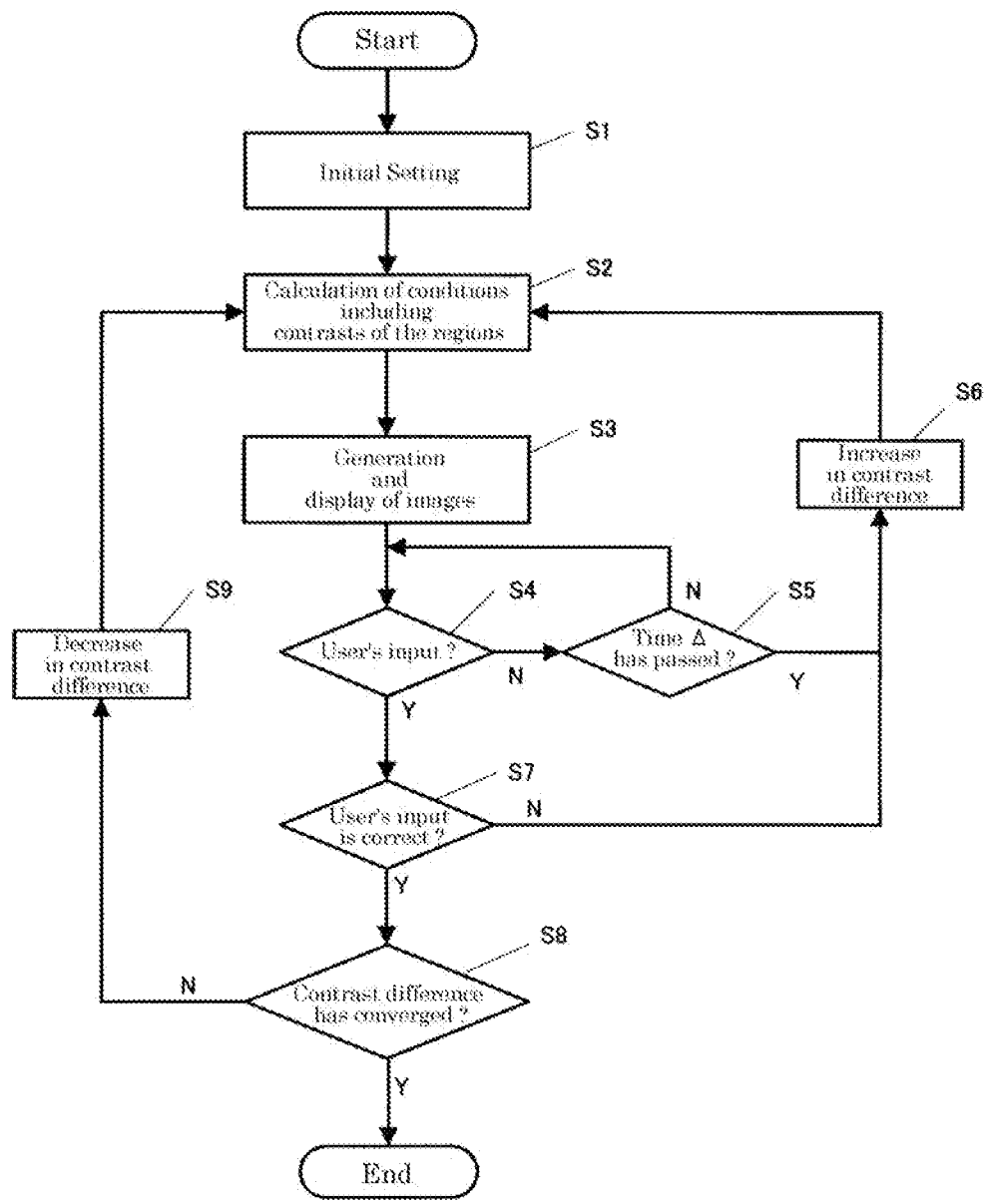
FIG. 5 A flow chart showing an operation of a flicker perception threshold measurement device according to a First Embodiment of the present invention.

The operation of the measurement device according to the First Embodiment of the present invention is more specifically described below. FIG. 5 is a flow chart showing an operation of a measurement device according to the First Embodiment of the present invention. In the following description, all operations are explained as being carried out by the CPU 1, unless otherwise specified. It is also assumed that the CPU 1 reads out necessary data (including programs) as required from the ROM 2 and the recording unit 4, processes the data using a predetermined area of the RAM 3 as work area, and stores the temporary results and the final processing results in the recording unit 4, if necessary; the initial condition required for the measurement is stored beforehand in the recording unit 4.

First, a menu is displayed on the display screen to allow the test subject 10 to select whether to carry out the measurement. When the test subject 10 operates the operating unit 9 to carry out the measurement, the following steps are performed.

In Step S1, the initial settings are made. For ease of explanation, the image contrast is explained as a luminance value. As the initial settings, the image-type information including the shape and size of the image having multiple regions, the ON period initial luminance value $L_{ON}$, the initial luminance value difference (contrast difference) $\Delta L$, and a time $\Delta$ for turning on and off an image in one type of contrast condition, are read out from the recording unit 4.

Figure 6:
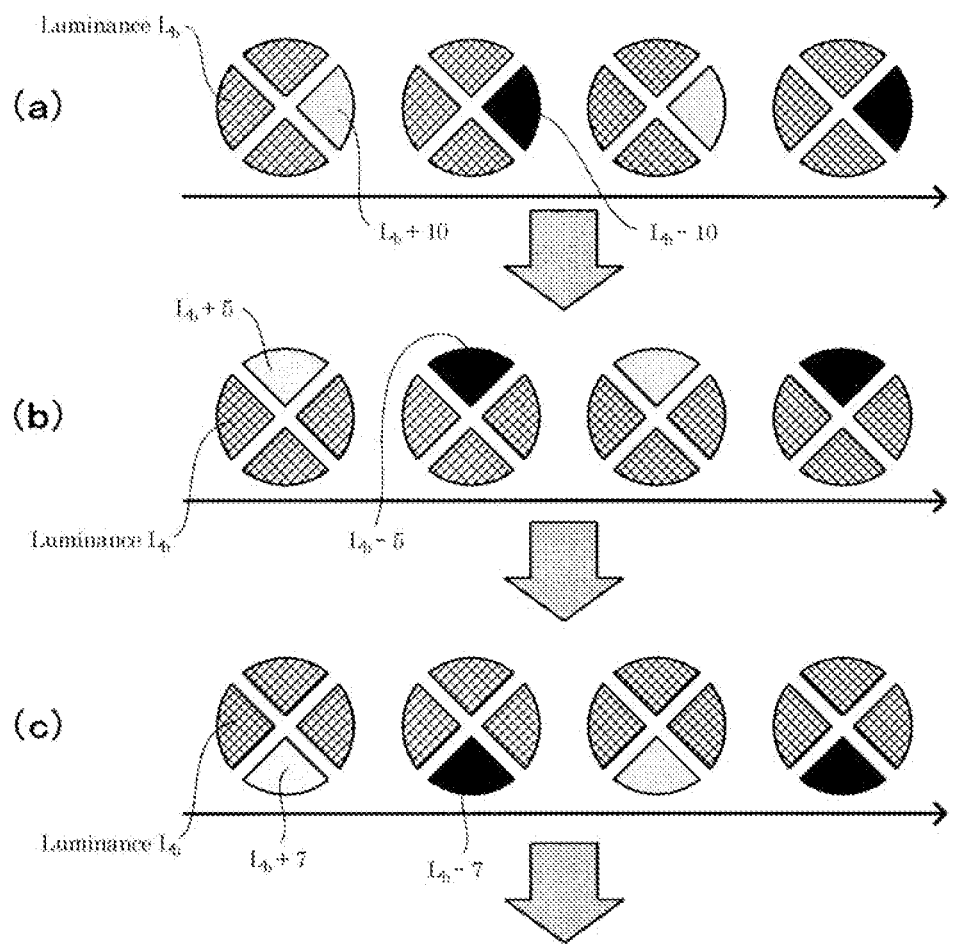
FIG. 6 A drawing showing changes in contrast difference.

The following example uses, as an example of the image, a circle consisting of four quarter-sector regions as shown in FIG. 6.

In Step S2, the various condition values for image data generation are calculated. More specifically, among the multiple regions, a flicker region to be displayed with a contrast difference is randomly determined, and this region is stored in RAM 3 as region information. For example, in the example of FIG. 6(a), the right quarter-sector corresponds to the flicker region, and the upper, lower, and left quarter-sectors correspond to reference regions in which flicker is not generated. The reference regions have, for example, an intermediate luminance value. In this example, the positions of the upper, lower, left, and right quarter-sectors are stored in RAM 3 as region information, for example, and are associated with values from 1 to 4. Then, $L_1(=L_{ON})$, $L_b(=L_1-\Delta L/2)$, $L_2(=L_1-\Delta L)$ are calculated, wherein $L_b$ represents the greater luminance value in the flicker region, $L_b$ represents the intermediate luminance value in the reference region, and $L_2$ represents the smaller luminance value in the flicker region.

Finally, before starting the next Step S3, time data is acquired from the clock unit 5. This time data is determined as a start time T.

In Step S3, an image is generated according to the conditions, such as the luminance value, determined in Step S2, and the image is displayed on the display unit 8. In the example of FIG. 6(a), a data item of an image having four regions with respective luminance values $L_b$, $L_b$, $L_b$, and $L_1$ and a data item of an image having four regions with respective luminance values $L_b$, $L_b$, $L_b$, and $L_2$ are alternately generated; and these images are alternately displayed in the display screen, corresponding to the ON and OFF states.

In Step S4, a judgment is made as to whether the test subject 10 operates the operation unit 9. For example, in Step S3, a text message that reads "Press one of the keys ↑, ↓, ←, and → corresponding to the flicker region when flickering begins" or the like may be displayed on the display screen before the display of the image begins. If the test subject 10 presses a key as they perceive a flicker in one of the multiple regions of the displayed image, the sequence goes to Step S7. If the key is not pressed by the test subject 10, the sequence goes to Step S5.

In Step S5, the current time t is acquired from the clock unit 5 to be compared with the start time T. If the difference (t−T) is smaller than the time Δ (t−T<Δ), the sequence goes back to Step S4. If the difference (t−T) is equal to or greater than the time Δ (t−T≥Δ), the sequence goes to Step S6. As such, until one of the keys ↑, ↓, ←, and → is pressed by the test subject 10, the display is continued in the same contrast condition (luminance condition) for the time Δ.

While judging that the test subject 10 is unable to perceive a flicker in the current contrast condition in Step 6, the sequence goes back to Step S2 to start image display and perception in the new contrast condition. More specifically, if one of the keys is not pressed by the test subject 10 within a predetermined time, it is judged that the perception and operation are not properly performed. Accordingly, the contrast difference ΔL is increased by a predetermined value D1. For example, in the example of FIG. 6(b) on the condition ΔL=2×5=10, if the perception is not properly performed, the contrast difference is increased by 4(D1=4). As a result, the image generation, display, and perception are performed again in the condition ΔL=2×7=14 as shown in FIG. 6(c).

In Step S7, a judgment is made as to whether the region indicated by the key pressed by the test subject 10 is identical to the region information stored in the RAM 3. When they are not identical, that is, when a wrong key is pressed, the sequence goes back to Step S6. When they are identical, that is, when the right key is pressed, the sequence goes to Step S8.

In Step S8, the contrast difference ΔL at the time is stored in the recording unit 4 as a measured contrast difference. Then, a judgment is made as to whether the difference between the measured contrast difference stored beforehand and the currently stored measured contrast difference is within a predetermined range. If, for example, the difference is within the predetermined range, the currently stored measured contrast difference is stored as a flicker perception threshold, and the sequence is ended. If the difference falls out of the predetermined range, the sequence goes to Step S9.

While judging that the fluctuation in flicker perception is too large in Step S9, the contrast difference ΔL is decreased by a predetermined value D2(D2>D1), and the sequence goes back to Step S2 to start image display and perception in a new contrast condition. For example, when the perception is properly performed under the condition ΔL=2×10=20 in FIG. 6(a), the contrast difference ΔL is decreased by 10(D2=10), i.e., the contrast difference ΔL is modified to the condition ΔL=2×5=10 in FIG. 6(b), and the image generation, display and perception are started again with this condition.

As explained above, through Steps S1 to S9, an image is presented to the test subject with a predetermined contrast condition during the time Δ, and a judgment is made to determine whether the operation by the test subject to notify the perception of a flicker is correct. By causing such irregular up-down variation in the contrast condition, more specifically, by varying the displayed image based on this true/false judgment, it is possible to gradually approximate the flicker perception of the test subject to a certain objective perception threshold, and thereby converge the threshold. In this manner, it is possible to objectively measure the flicker perception threshold of a specific test subject.

Accordingly, it is possible to determine whether the test subject is experiencing fatigue by measuring and recording a flicker perception threshold when the test subject is free from fatigue; then measuring a flicker perception threshold again for the same test subject in the same manner, and comparing the obtained flicker perception threshold with the value obtained when the test subject was free from fatigue.

The present invention is not limited to the above First Embodiment; and may be altered, for example, by varying the flow chart shown in FIG. 5.

Specifically, although the above embodiment increases and decreases the contrast difference ΔL in two stages (D2>D1) depending on the true/false judgment, for example, it is also possible to vary the contrast difference ΔL in more multiple stages, thereby controlling the contrast difference ΔL so that a large value is set in the beginning of the measurement and the value is gradually decreased as the measurement proceeds. As such, in addition to the up-down variation in the above embodiment, the contrast difference ΔL may also be controlled using other psychophysical methods for determining a perception threshold. In this case, the flicker threshold may be determined by averaging the values of measured contrast difference recorded in the several latest measurements. It is also possible to unify the variation amount of the contrast difference ΔL (i.e., D1=D2, for example, 2), though it prolongs the measurement.

The shape and size (number of pixels) of the image to be displayed may be arbitrarily determined. For example, as in the image shown in FIG. 7, the region corresponding to the number may be determined as the flicker region while determining the remaining area as a reference region. In this case, if the contrast difference is too small, the number cannot be identified. Therefore, in this case, by creating a visual stimulation using the contrast difference between the number and the background, and carrying out a judgment as to whether the test subject notifies the perception by pressing a key corresponding to the number, it is also possible to carry out the measurement of flicker perception threshold of a test subject as in the above embodiment. In this case, the value corresponding to the number shown in the display may be used as the region information. FIG. 8 shows another example. In this example, one of the seven regions of the image is determined as the flicker region, while determining the remaining area as a reference region. As in the First Embodiment above, by carrying out a judgment as to whether the test subject properly specifies the flicker region, it is possible to measure a flicker perception threshold of the test subject.

Moreover, instead of the real-time image generation by the CPU 1, it is also possible to read out image data previously generated and stored in the recording unit 4, as required.

Furthermore, although the contrast in the reference region is identical to the intermediate value between the two different contrasts in the above embodiment, it is also possible to perform the measurement of a flicker perception threshold as above using an arbitrary value for the contrast in the reference region. However, the contrast in the reference region is preferably identical to the intermediate value of the contrast difference. It is also possible to generate the contrast difference by changing the color of the displayed image. Further, in a method adopting a procedure to set a large initial contrast difference and then decrease the contrast difference, it is possible to determine the measured contrast difference at which the test subject stops perceiving the flicker as the flicker perception threshold.

Second Embodiment

The fundamental structure of the measurement device according to the Second Embodiment is the same as the measurement device (FIG. 3) in the First Embodiment, except that the flicker display is performed in multiple regions of the display screen of the display unit 8 at different blinking frequencies. More specifically, instead of changing the contrast difference of an image to be presented to the test subject using a display screen, this device changes the blinking frequency.

In the Second Embodiment, a visual stimulation is generated by blinking one of the regions in the display screen at a first blinking frequency that falls within a blinking frequency range perceivable by human. Further, the device also causes the remaining area of the display screen to blink at a second blinking frequency that falls within a blinking frequency range unnoticeable by human (including 0 Hz, at which the image is not blinked); more specifically, the device causes the remaining area of the display screen to blink at a blinking frequency, which appears as a continuous ON state. The device records the region information regarding the region (visual stimulation region) that blinks at the first blinking frequency, carries out a judgment as to whether the test subject properly reacts to the flicker perception based on the region information, and then varies the first blinking frequency and the blinking visual stimulation region in the image according to the true/false judgment regarding the reaction of the test subject. Further, to vary the visual stimulation region, a perception threshold determination method in which the value converges to the perception threshold is employed. This eliminates arbitrariness and inclination of the test subject during the test, thereby carrying out a measurement of flicker threshold in a short time based on objective flicker perception.

The Second Embodiment is essentially based on the same control principle as that of the First Embodiment. Therefore, in the following explanation, only the steps different from those in the First Embodiment are described.

The following briefly describes the operation of the measurement device according to the Second Embodiment. The CPU 1 randomly specifies a predetermined region as region information in an image having two or more regions and stores the information in the RAM 3, and then causes the predetermined region to blink at the first blinking frequency while causing the remaining area of the display screen to blink at the second blinking frequency. The test subject 10 observes the image displayed on the display screen of the display unit 8, and operates the operation unit 9 to specify a certain region in the image when they recognize the appearance or disappearance of a flicker in the region. This operation information is sent to the CPU 1 via the IF unit 6, and is recorded in the RAM 3 or the recording unit 4. The CPU 1 carries out a judgment as to whether the region specified by the test subject is identical to the predetermined region stored as the region information. When they are identical, in other words, when the test subject properly specifies a flicker region, the CPU 1 generates an image again by increasing the first blinking frequency, and displays the image to the test subject. When they are not identical, in other words, when the test subject improperly specifies a flicker region, the CPU 1 generates an image again by decreasing the first blinking frequency, and displays the image to the test subject.

As such, a judgment is carried out as to whether the test subject properly perceives a flicker by irregularly changing the image display state. In the present invention, instead of monotonously increasing or decreasing the blinking frequency and storing the blinking frequency at the time when the test subject perceives a flicker as in the prior art, the first blinking frequency and a flicker region are irregularly changed, and the convergence value of the first blinking frequency at which the condition where the test subject perceives the appearance or disappearance of flicker is stably converged is determined as a flicker perception threshold.

Figure 9:
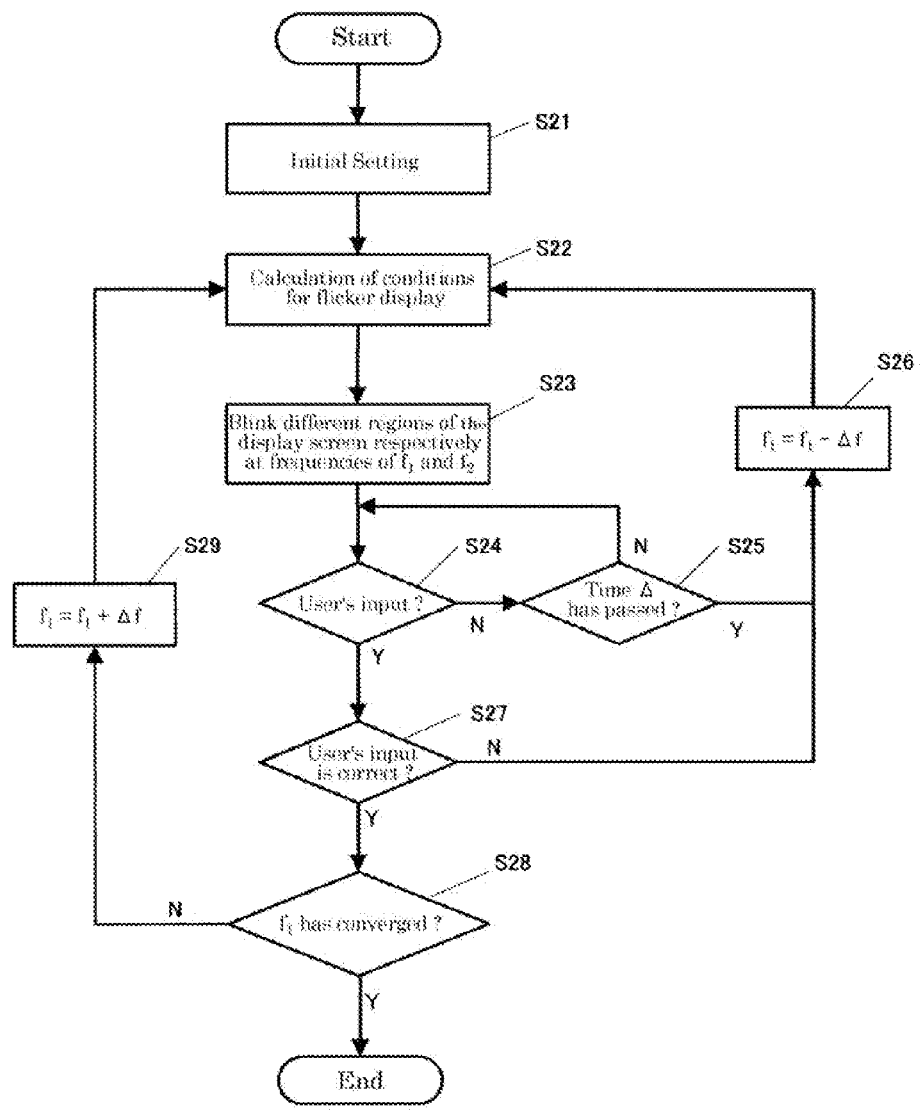
FIG. 9 A flow chart showing an operation of a flicker perception threshold measurement device according to a Second Embodiment of the present invention.

The operation of the measurement device according to the Second Embodiment of the present invention is more specifically described below. FIG. 9 is a flow chart showing an operation of a measurement device according to the Second Embodiment of the present invention.

First, a menu is displayed on the display screen of the display unit 8 to allow the test subject 10 to select whether to carry out the measurement. When the test subject 10 operates the operating unit 9 to carry out the measurement, the following steps are performed.

Figure 7:
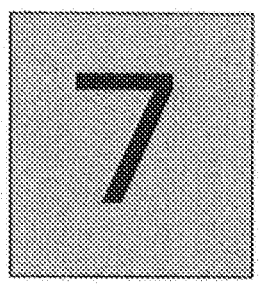
FIG. 7 A drawing showing an example of a displayed image.
Figure 8:
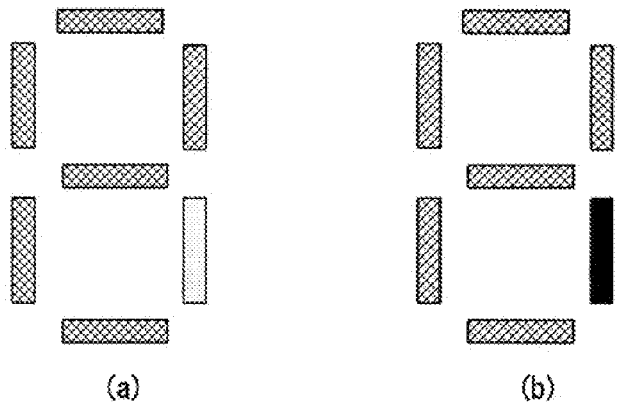
FIG. 8 A drawing showing examples of displayed image.

The following example uses the image shown in FIG. 7 that consists of a region representing a number and a background region, as an example of the flicker region.

In Step S21, the initial settings are made. Specifically, a variety of information including the type, shape and position of the flicker region, the initial value of the first blinking frequency $f_1$, the initial value of the variation range $\Delta f$ of the first blinking frequency, the second blinking frequency $f_2$, and a time $\Delta$ as a duration for blinking a display screen with a certain blinking frequency condition are read out from the recording unit 4. Here, the initial value of $f_1$ may be $f_2$.

In Step S22, the various conditions for flicker display are calculated. More specifically, a single-digit number to be displayed at the first blinking frequency is randomly determined, and is stored in RAM 3 as region information. Then, first image data corresponding to the flicker region for showing the number, and second image data corresponding to the background region where no flicker is displayed are generated. Here, $f_1$ represents the first blinking frequency for the flicker region, and $f_2$ represents the second blinking frequency for the background region.

Finally, before starting the next Step S23, time data is acquired from the clock unit 5. This time data is referred to as a start time T.

In Step S23, according to the blinking conditions determined in Step S22, the device causes the region corresponding to the randomly set single digit number to blink at the first blinking frequency $f_1$, and causes the background region to blink at the second blinking frequency $f_2$. More specifically, the first image data is displayed on the display screen at the first blinking frequency $f_1$, and the second image data is displayed on the display screen at the second blinking frequency $f_2$.

In Step S24, a judgment is made as to whether the test subject 10 operates the operation unit 9. For example, in Step S23, a text message that reads "Press the key of the number shown" or the like is displayed on the display screen before the display screen starts blinking. If the test subject 10 presses one of the keys 0 to 9 as they perceive the flicker display of the number, the sequence goes to Step S27. If the key is not pressed by the test subject 10, the sequence goes to Step S25.

In Step S25, the current time t is acquired from the clock unit 5 to be compared with the start time T. If the difference $(t-T)$ is smaller than the time $\Delta$ $(t-T<\Delta)$, the sequence goes back to Step S24. If the difference $(t-T)$ is equal to or greater than the time $\Delta$ $(t-T \geq \Delta)$, the sequence goes to Step S26. As such, until one of the keys is pressed by the test subject 10, the display is continued in the same blinking condition for the time $\Delta$.

While judging that the test subject 10 is unable to perceive a flicker with the current first blinking frequency $f_1$ in Step 26, the first blinking frequency $f_1$ is decreased by $\Delta f$ and the sequence goes back to Step S22 to start image display and perception in the new contrast condition. More specifically, if one of the keys is not pressed by the test subject 10 within a predetermined time, it is judged that the perception and operation are not properly performed.

In Step S27, a judgment is made as to whether the number indicated by the key pressed by the test subject 10 is identical to the stored region information. When they are not identical, that is, when a wrong key is pressed, the sequence goes back to Step S26. When they are identical, that is, when the right key is pressed, the sequence goes to Step S28.

In Step S28, the first blinking frequency $f_1$ at the time is stored in the recording unit 4 as a measurement frequency. Then, a judgment is made as to whether the difference between the measurement frequency stored beforehand and the currently stored measurement frequency is within a predetermined range. If the difference is within the predetermined range, for example, the currently stored measurement frequency is stored as a flicker perception threshold, and the sequence is ended. If the difference falls out of the predetermined range, the sequence goes to Step S29.

While judging that the fluctuation in flicker perception is too large in Step S29, the first blinking frequency $f_1$ is decreased by $\Delta f$, and the sequence goes back to Step S22 to start the blinking of the display screen of the display unit 8 in the new blinking condition to allow the test subject to perform the perception.

As explained above, through Steps S21 to S29, an image is presented to the test subject in a predetermined flicker condition during the time $\Delta$, and a judgment is made as to whether the operation by the test subject to notify the perception of a flicker is correct. With such irregular up-down variation of the first blinking frequency and irregular variation of the region that blinks at the blinking frequency based on this true/false judgment, it is possible to converge the flicker perception threshold to a certain objective perception threshold. In this manner, it is possible to objectively measure the flicker perception threshold of a specific test subject.

The present invention is, of course, not limited to the above Second Embodiment; and may be altered, for example, by changing the flow chart shown in FIG. 9.

Specifically, it is possible to vary the variation range $\Delta f$ of the first blinking frequency; more specifically, it is possible to control $\Delta f$ so that a large value is set in the beginning of the measurement and that the value is gradually decreased as the measurement proceeds. The value of $f_1$ may be converged using various psychophysical methods for determining a perception threshold. Further, the blinking region displayed in the display screen may be varied in many ways as shown in FIG. 6 and FIG. 8. Furthermore, when a control method in which a small first blinking frequency is set in the beginning of the measurement and the value is gradually increased, it is possible to determine the first blinking frequency at which the test subject stops perceiving the flicker as the flicker perception threshold.

In addition, although the above Second Embodiment performs flicker display using a display screen, it is also possible to use a display device comprising a plurality of LED groups, thereby generating a flicker using these LEDs instead of a display screen. Each LED group may comprise single or plural LEDs.

Further, although the CPU 1 generates the image data in real time in the above Second Embodiment, it is also possible to read out image data previously generated and stored in the recording unit 4; i.e., it is possible to read out a set of plural image data items showing a single-digit number, and a corresponding set of image data showing the background from the recording unit 4.

Although the program for measuring the degree of mental fatigue is stored beforehand in the ROM 2 in the above First and Second Embodiments, it is also possible to download the program to the measurement device by accessing an Internet server, or installing the program in the measurement device via a detachable recording medium, such as a memory card.

The features of the present invention are more specifically described below in reference to Examples.

EXAMPLE 1

A personal computer (PC, hereinafter) having a liquid crystal screen that refreshes the display at 30 Hz was implemented with a program for carrying out the method of the present invention. Using the PC, image data was generated by temporally or spatially varying the normalized contrast of a stimulation object (image), thereby displaying a black background in the screen. An experiment was performed by carrying out a true/false judgment as to whether the test subject properly perceives the flicker, and finding the time point at which the perception by the test subject was stably ended.

An image in which the four quarter-sectors are disposed in a circle having a 10-pixel diameter, as shown in FIG. 6, was used as the stimulation, i.e., the image to be presented to the test subject. When the test subject perceived a flicker, they pressed one of the arrow keys ($\uparrow$, $\downarrow$, $\leftarrow$, $\rightarrow$) corresponding to the flicker region. The time $\Delta$, which is a predetermined time during which the presence or absence of push-button operation is judged, was 3 s (seconds).

As shown in FIG. 2, the normalized contrast was $L_{OFF}/L_{ON}$, which is a ratio of the luminance value ($L_{OFF}$) of the OFF pixel to the luminance value ($L_{ON}$) of the ON pixel. Further, during the experiment, the luminance value $L_{ON}$ of the ON pixel was fixed to 255 (the maximum value for 8-bit). More specifically, the greater one of the luminance value (luminance value $L_1$) was fixed to 255. Further, the initial contrast difference $\Delta L$ was set to a luminance of 1 gradation. Accordingly, the initial intermediate luminance value $L_b$ in the three regions with no flicker was $(L_1-\Delta L/2=255-\frac{1}{2}=)$ 254.5. The smaller one of the luminance values (luminance value $L_2$) was $(L_1-\Delta L=255-1=)$ 254. Accordingly, the initial normalized contrast was about 0.996 (254/255=).

With these conditions, a typical test subject performed a single operation of flicker perception threshold measurement. More specifically, with these initial conditions, an image was generated by temporally switching the luminance value of an arbitrarily-selected region between $L_1$ and $L_1-\Delta L$, and setting the luminance value of the other three regions to $L_1-\Delta L/2$; the generated image was presented to the test subject. When the test subject was unable to perceive a flicker within a predetermined time (3 s), or when the reaction (keystroke) of the test subject to notify the perception was judged to be improper, the normalized contrast was decreased by $\frac{1}{255}$ (the contrast difference $\Delta L$ was increased by 1 gradation) so as to allow the test subject to more easily perceive a flicker, and an image of a new randomly-selected flicker region was generated and presented to the test subject. On the other hand, when the reaction (keystroke) of the test subject to notify the perception was judged to be proper within a predetermined time, the contrast difference $\Delta L$ was stored in the recording unit 4, the normalized contrast was increased by $\frac{1}{255}$ (the contrast difference $\Delta L$ was decreased by 1 gradation) so as to make the flicker perception by the test subject more difficult; and an image of a new, randomly selected flicker region was generated and presented to the test subject. As such, the normalized contrast (i.e., contrast difference ΔL) and the flicker region were repeatedly changed according to the true/false judgment of the flicker perception by the test subject until the normalized contrast stably reached a certain threshold.

Figure 10:
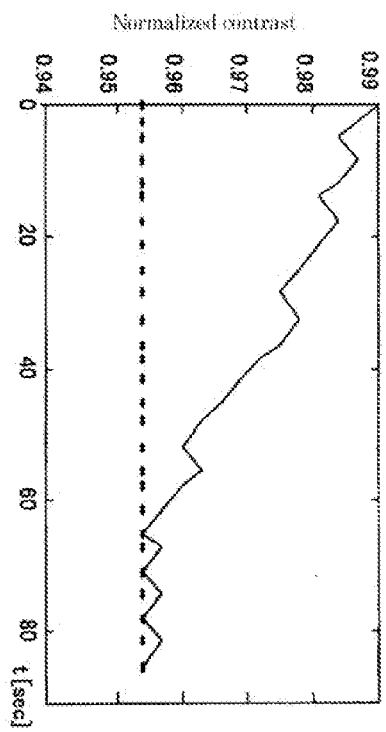
FIG. 10 A drawing showing a convergence state of a normalized contrast in measurement of flicker perception threshold of a typical test subject.

FIG. 10 is a drawing showing a convergence state of the normalized contrast in a single measurement of flicker perception threshold of a typical test subject. The horizontal axis represents a measurement time (seconds) elapsed since the examination was started. The vertical axis represents the normalized contrast.

As shown in FIG. 10, the normalized contrast moved from the upper left of the figure, where the flicker perception cannot be perceived, to the lower right, and gradually approached the flicker perception threshold of the test subject. The keystroke accuracy rate was determined to be 50/50 when the normalized contrast was about 0.957 and the contrast difference ΔL was 10.965. At this point, the measurement was ended, and it was judged that the perception was stably converged. Accordingly, in this measurement example, the flicker perception threshold of the test subject was determined to be 0.957. The time taken to the measurement was about 80 sec.

Such measurement of the normalized contrast at which the test subject starts perceiving a flicker without arbitrariness or inclination enabled objective evaluation of the fatigue degree. Further, although it is not shown, the flicker perception threshold obtained for the same test subject was stable. This also confirmed that the present invention can eliminate arbitrariness in key operation of the test subject, unlike the hitherto known measurement device that cannot ensure stability of the obtained threshold.

Moreover, in the hitherto known measurement device, the measurement, which took 20 to 30 s, was performed five times, and a flicker perception threshold was found by averaging the five measurement values; therefore, the entire measurement took 2 to 3 minutes for each test subject. In contrast, the measurement of the present invention takes about 60 to 90 sec., as is evident from the present example, in which it took 80 sec. As such, the measurement time was desirably reduced.

EXAMPLE 2

To evaluate the reliability of the present invention, the measurement result of the present invention was compared with the measurement result of a hitherto known flicker measurement device. As in Example 1 above, the normalized contrast of the stimulation was temporally and spatially varied, and observation of how the normalized contrast (corresponding to the flicker value), which is a flicker perception threshold, changes depending on the fatigue load was performed. In this evaluation, the test subject had a fatigue load caused by all-night labor that continued from late evening to the next afternoon, and the normalized contrast of a stimulation (image) displayed on a display screen was varied using a PC, thereby measuring the flicker perception threshold.

The evaluation is specifically described below. The test subject was a healthy adult. The test subject had designated intermittent daytime labor before the evaluation; therefore, the test subject already had a certain level of fatigue at the beginning of the evaluation. The first measurement was carried out at 2:30 a.m. The flicker perception threshold was measured using the respective measurement methods of the known flicker measurement device and the present invention. Thereafter, the test subject had 6 more hours of designated labor. The second measurement of flicker perception threshold was carried out at 8:30 a.m. using the two measurement methods. Thereafter, the test subject had a meal and a short sleep. After six hours, i.e., at 2:30 p.m., the third measurement of flicker perception threshold was carried out. The flicker perception threshold was measured using a standard flicker device and a PC in this order. As described above, the measurement was performed three times.

The stimulation was presented in the same conditions as in Example 1 above. A MacBook Pro (Apple) was used as the PC. A Roken Digital Flicker Model RDF-1 (manufactured by Shibata Co., Ltd.) was used as the standard flicker device. A red stimulation target was displayed while decreasing the frequency from 55 Hz at a rate of 1 Hz per second.

Figure 11:
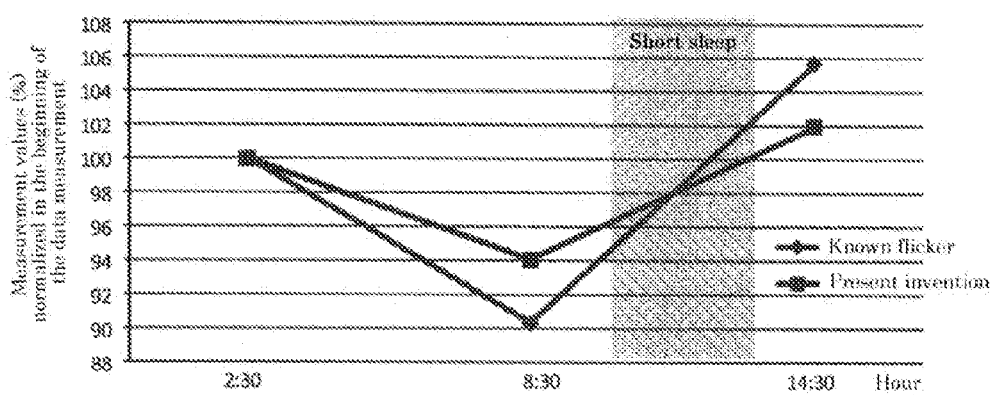
FIG. 11 A graph showing a measurement result of a flicker perception threshold of a test subject.

FIG. 11 is a graph showing a measurement result of a flicker perception threshold of a test subject. In this graph, the vertical axis presents the flicker perception thresholds normalized by the measurement values obtained at 2:30 p.m. More specifically, the measurement values obtained at 2:30 p.m. are set to 100, and the values obtained thereafter in proportion to 100 are plotted.

The graph reveals that the flicker perception thresholds measured in the above two methods became lowest in the measurement at 8:30 a.m. when the test subject had maximum fatigue. The graph also reveals that, after the test subject had a short sleep, both of the flicker thresholds measured in the above two methods recovered and became higher than those measured at 2:30 a.m. Further, when the values measured in the two methods are normalized with their variation ranges, respectively, in other words, when the maximum value and the minimum value are plotted within the same width, the flicker thresholds show substantially the same tendency. Accordingly, it can be assumed that the changes in measurement values obtained by the standard flicker device were substantially duplicated in the measurement values obtained by a PC.

As described, it was confirmed that the flicker perception thresholds measured in the above two methods were decreased by a fatigue load caused by all-night labor, and that the fatigue was recovered by taking a short sleep break. It was also shown that the flicker perception thresholds measured according to the method of the present invention reflected the fatigue conditions, as with the flicker values measured by the know method.

INDUSTRIAL APPLICABILITY

The present invention is able to objectively evaluate a flicker perception threshold and the fatigue of a test subject by using a computer or a mobile phone with ordinary functions, or by using a dedicated device. The present invention prevents arbitrary control of the measurement result, thereby obtaining an objective measurement result. With this advantage, the present invention is useful for appropriate health-care management and prevention of industrial accidents and injuries/illness at production sites.

REFERENCE NUMERALS

1 Arithmetic processing unit (CPU)
2 Read-only memory (ROM)
3 Rewritable memory (RAM)
4 Recording unit
5 Clock unit
6 Interface unit (IF unit)
7 Internal bus
8 Display unit
9 Operation unit

The invention claimed is:

1. A method for measuring a flicker perception threshold using a device comprising an operation unit, a display screen, and a recording unit, the method comprising:

a first step of alternately displaying on the display screen an ON-period image and an OFF-period image each having a plurality of regions, the ON-period image and the OFF-period image having a contrast difference only in one corresponding region selected from the plurality of regions;

a second step of, when it is judged during display of the ON and OFF-period images that an operation in the operation unit that is made by a test subject in response to perception of a flicker does not properly specify the one corresponding region, increasing the contrast difference, and when it is judged that the operation in the operation unit properly specifies the one corresponding region, recording the contrast difference at the time in the recording unit as a measured contrast difference; and a third step of judging whether the measured contrast difference recorded in the recording unit is converged; when it is judged that the measured contrast difference is not converged, decreasing the contrast difference, and when it is judged that the measured contrast difference is converged, determining a convergence value of the measured contrast difference as information corresponding to the flicker perception threshold.

2. A method for measuring a flicker perception threshold using a device comprising an operation unit, a display screen, and a recording unit, the method comprising:

a first step of blinking one region selected from a plurality of regions of the display screen at a first blinking frequency, and blinking other regions of the display screen at a second blinking frequency that cannot be perceived by human, a second step of, when it is judged during the blinking that an operation in the operation unit that is made by a test subject in response to perception of a flicker in the display screen does not properly specify the one region, decreasing the first blinking frequency, and when it is judged that the operation in the operation unit properly specifies the one region, recording the first blinking frequency at the time in the recording unit as a measured blinking frequency; and a third step of judging whether the measured blinking frequency recorded in the recording unit is converged; when it is judged that the measured blinking frequency is not converged, increasing the first blinking frequency, and when it is judged that the measured blinking frequency is converged, determining a convergence value of the measured blinking frequency as information corresponding to the flicker perception threshold.

3. A method for measuring a flicker perception threshold using a device comprising an operation unit, a plurality of groups of one or more light-emitting elements disposed in a plurality of regions, and a recording unit, the method comprising:

A first step of blinking one or more light-emitting elements disposed in a region selected from the plurality of regions at a first blinking frequency, and blinking other light-emitting elements at a second blinking frequency that cannot be perceived by human, a second step of, when it is judged during the blinking that an operation in the operation unit that is made by a test subject in response to perception of a flicker of the light-emitting elements does not properly specify the one or more light-emitting elements in the region, decreasing the first blinking frequency, and when it is judged that the operation in the operation unit properly specifies the one or more light-emitting elements in the region, recording the first blinking frequency at the time in the recording unit as a measured blinking frequency; and a third step of judging whether the measured blinking frequency recorded in the recording unit is converged; when it is judged that the measured blinking frequency is not converged, increasing the first blinking frequency, and when it is judged that the measured blinking frequency is converged, determining a convergence value of the measured blinking frequency as information corresponding to the flicker perception threshold.

4. The method according to claim 1, wherein the plurality of regions are separated from each other.

5. The method according to claim 1, wherein the one region selected from the plurality of regions represents a number or a graphic, and the step of specifying the region is a step of specifying the number or the graphic.

6. A device comprising an arithmetic processing unit, a display screen, an operation unit, and a recording unit, wherein:

the arithmetic processing unit alternately displays on the display screen an ON-period image and an OFF-period image each having a plurality of regions, the ON-period image and the OFF-period having a contrast difference only in one corresponding region selected from the plurality of regions;

when it is judged during display of the ON and OFF-period images that an operation in the operation unit that is made by a test subject in response to perception of a flicker does not properly specify the one corresponding region, the arithmetic processing unit increases the contrast difference, and when it is judged that the operation in the operation unit properly specifies the one corresponding region, the arithmetic processing unit records the contrast difference at the time in the recording unit as a measured contrast difference; and the arithmetic processing unit judges whether the measured contrast difference recorded in the recording unit is converged; when it is judged that the measured contrast difference is not converged, the arithmetic processing unit decreases the contrast difference, and when it is judged that the measured contrast difference is converged, the arithmetic processing unit determines a convergence value of the measured contrast difference as information corresponding to the flicker perception threshold.

7. A device comprising an arithmetic processing unit, a display screen, an operation unit, and a recording unit, wherein:

the arithmetic processing unit blinks the one region selected from a plurality of regions of the display screen at a first blinking frequency, and blinks other regions at a second blinking frequency that cannot be perceived by human, when it is judged during the blinking that an operation in the operation unit that is made by a test subject in response to perception of a flicker in the display screen does not properly specify the one region, the arithmetic processing unit decreases the first blinking frequency, and when it is judged that the operation in the operation unit properly specifies the one region, the arithmetic processing unit records the first blinking frequency at the time in the recording unit as a measured blinking frequency; and the arithmetic processing unit judges whether the measured blinking frequency recorded in the recording unit is converged; when it is judged that the measured blinking frequency is not converged, the arithmetic processing unit increases the first blinking frequency, and when it is judged that the measured contrast difference is converged, the arithmetic processing unit determines a convergence value of the measured blinking frequency as information corresponding to the flicker perception threshold.

8. A device comprising an arithmetic processing unit, an operation unit, a plurality of groups of one or more light-emitting elements disposed in a plurality of regions, and a recording unit, wherein:

the arithmetic processing unit blinks one or more light-emitting elements disposed in the region selected from the plurality of regions at a first blinking frequency, and blinking other light-emitting elements at a second blinking frequency that cannot be perceived by human, when it is judged during the blinking that an operation in the operation unit that is made by a test subject in response to perception of a flicker of the light-emitting elements does not properly specify the one or more light-emitting elements in the region, the arithmetic processing unit decreases the first blinking frequency, and when it is judged that the operation in the operation unit properly specifies the one or more light-emitting elements in the region, the arithmetic processing unit records the first blinking frequency at the time in the recording unit as a measured blinking frequency; and the arithmetic processing unit judges whether the measured blinking frequency recorded in the recording unit is converged; when it is judged that the measured blinking frequency is not converged, the arithmetic processing unit increases the first blinking frequency, and when it is judged that the measured blinking frequency is converged, the arithmetic processing unit determines a convergence value of the measured blinking frequency as information corresponding to the flicker perception threshold.

9. The device according to claim 6, wherein the plurality of regions are separated from each other.

10. The device according to claim 6, wherein the one region selected from the plurality of regions represents a number or a graphic, and the step of specifying the region is a step of specifying the number or the graphic.

11. The method according to claim 2, wherein the plurality of regions are separated from each other.

12. The method according to claim 3, wherein the plurality of regions are separated from each other.

13. The method according to claim 2, wherein the one region selected from the plurality of regions represents a number or a graphic, and the step of specifying the region is a step of specifying the number or the graphic.

14. The method according to claim 3, wherein the one region selected from the plurality of regions represents a number or a graphic, and the step of specifying the region is a step of specifying the number or the graphic.

15. The device according to claim 7, wherein the plurality of regions are separated from each other.

16. The device according to claim 8, wherein the plurality of regions are separated from each other.

17. The device according to claim 7, wherein the one region selected from the plurality of regions represents a number or a graphic, and the step of specifying the region is a step of specifying the number or the graphic.

18. The device according to claim 8, wherein the one region selected from the plurality of regions represents a number or a graphic, and the step of specifying the region is a step of specifying the number or the graphic.

* * * * *